United States Patent [19]

Griffin et al.

[11] Patent Number: 5,153,514
[45] Date of Patent: Oct. 6, 1992

[54] ANTENNA AND WEAR PLATES FOR BOREHOLE LOGGING APPARATUS

[75] Inventors: Douglas D. Griffin, Bethel; Robert L. Kleinberg, Ridgefield; Abdurrahman Sezginer, Brookfield, all of Conn.; Masafumi Fukuhara, Sagamihara, Japan

[73] Assignee: Schlumberger Technology Corp., New York, N.Y.

[21] Appl. No.: 657,710

[22] Filed: Feb. 19, 1991

[51] Int. Cl.$^5$ .......................................... G01R 33/20
[52] U.S. Cl. .................................................... 324/303
[58] Field of Search ............... 324/300, 303, 307, 318, 324/322

[56] References Cited

U.S. PATENT DOCUMENTS

| | | | |
|---|---|---|---|
| 3,597,681 | 8/1971 | Huckabay | 324/303 |
| 3,723,856 | 3/1973 | Brown | 324/303 |
| 4,652,829 | 3/1987 | Safinya | 324/338 |
| 4,710,713 | 12/1987 | Strikman | 324/318 |
| 4,717,876 | 1/1988 | Masi et al. | 324/303 |
| 4,717,877 | 1/1988 | Taicher et al. | 324/303 |
| 4,717,878 | 1/1988 | Taicher et al. | 324/303 |
| 4,933,638 | 6/1990 | Kenyon et al. | 324/303 |

OTHER PUBLICATIONS

W. G. Clark, "Pulsed Nuclear Resonance Apparatus", The Review of Scientific Instruments, vol. 35, No. 3, (Mar. 1964).
Dobbs, in W. P. Mason and R. N. Thurston, "Physical Acoustics Principles and Methods", vol. X, (1973), title page and pp. 127–191.
E. Kartheuser, L. R. Ram Mohan, and S. Rodriguez, "Theory of Electromagnetic Generation of Acoustic Waves in Metals", Advances In Physics, vol. 35, No. 5, 423–505, (1986), contents pp. 423, 424.
A. B. Przedpeiski, "Simplify Conjugate Bilateral Matching Of Complex Impedances. A Unified Approach Provides Practical L, Pi or T Solutions With A Low-Cost Programmable Calculator", Electronic Design 5, (Mar. 5, 1978).
J. S. Belrose, "Ferromagnetic Loop Aerials For Kilometric Waves", Wireless Engineer, vol. 32 N 2 pp. 41–46 (Feb. 1955).
M. L. Buegg and G. L. Peterson, "Acoustic Ringing Effects In Pulsed Nuclear Magnetic Resonance Probes", Rev. Sci. Instrum., vol. 49, No. 8, (Aug. 8, 1978).
E. Fukushima and S. B. W. Roeder "Spurious Ringing In Pulse NMR", Journal of Magnetic Resonance, 33, 199–203 (1979).

Primary Examiner—Michael J. Tokar
Attorney, Agent, or Firm—Martin M. Novack; Leonard W. Pojunas

[57] ABSTRACT

An apparatus is disclosed for investigating nuclear magnetic resonance properties of earth formations traversed by a borehole, including a logging device adapted for longitudinal movement in the borehole. The device includes a first subsystem for producing a static magnetic field in the formations and a second subsystem for transmitting electromagnetic energy into the formations and for detecting electromagnetic energy from the formations. The second subsystem comprises an antenna assembly which includes an open-ended shell formed of a magnetically permeable material. An open-ended electrically conductive body is disposed within the shell and is spaced therefrom. A medium whose acoustic impedance is substantially different than the acoustic impedance of the shell and the body is disposed between the shell and the body. An electrically conductive probe is disposed in the body, and an electrically insulating magnetically permeable loading material disposed in the body. The shell is formed of a material having a magnetic permeability that is high enough to render the magnetic reluctance of the loading material several times the magnetic reluctance of the shell. The body is formed of a metal having thickness that is at least several skin depths in said metal at the frequency of the electromagnetic energy and is less than the minimum thickness that would support an acoustic resonance mode in its thickness direction at the frequency of the electromagnetic energy. The apparatus provides a shunt path for the static magnetic field in the region of the antenna that would otherwise have a deleterious effect on the loading material of the antenna and on antenna operation. The apparatus also minimizes undesirable ringing of the antenna.

50 Claims, 9 Drawing Sheets

ANTENNA AND WEAR PLATES FOR BOREHOLE LOGGING APPARATUS

FIELD OF THE INVENTION

This invention relates to apparatus for measuring characteristics of formations surrounding earth boreholes and, more particularly, to an antenna and wear plates for such apparatus.

BACKGROUND OF THE INVENTION

In well logging of earth boreholes there exist applications where it is necessary to accurately measure, in a hostile and noisy environment, very small electromagnetic signals. One such application, which has had limited practical success to date, is a logging device which measures nuclear magnetic resonance ("NMR") properties of earth formations. It has been recognized that particles of a formation having magnetic spin, for example atomic nuclei, protons, or electrons, have a tendency to align with a static magnetic field $B_0$ which is imposed on the formation. If a pulse of alternating current having a frequency f is passed through a transmitter coil, producing an oscillating polarizing field $B_1$ perpendicular to the static field $B_0$, a population of protons in a formation would be tipped away from the static field direction. At the end of the pulse, when $B_1$ is removed, the protons precess about the $B_0$ vector. After a characteristic time called the longitudinal or spin-lattice relaxation time $T_1$, the protons have relaxed to thermal equilibrium, wherein a percentage of protons are aligned in the direction of $B_0$.

Figure 1:
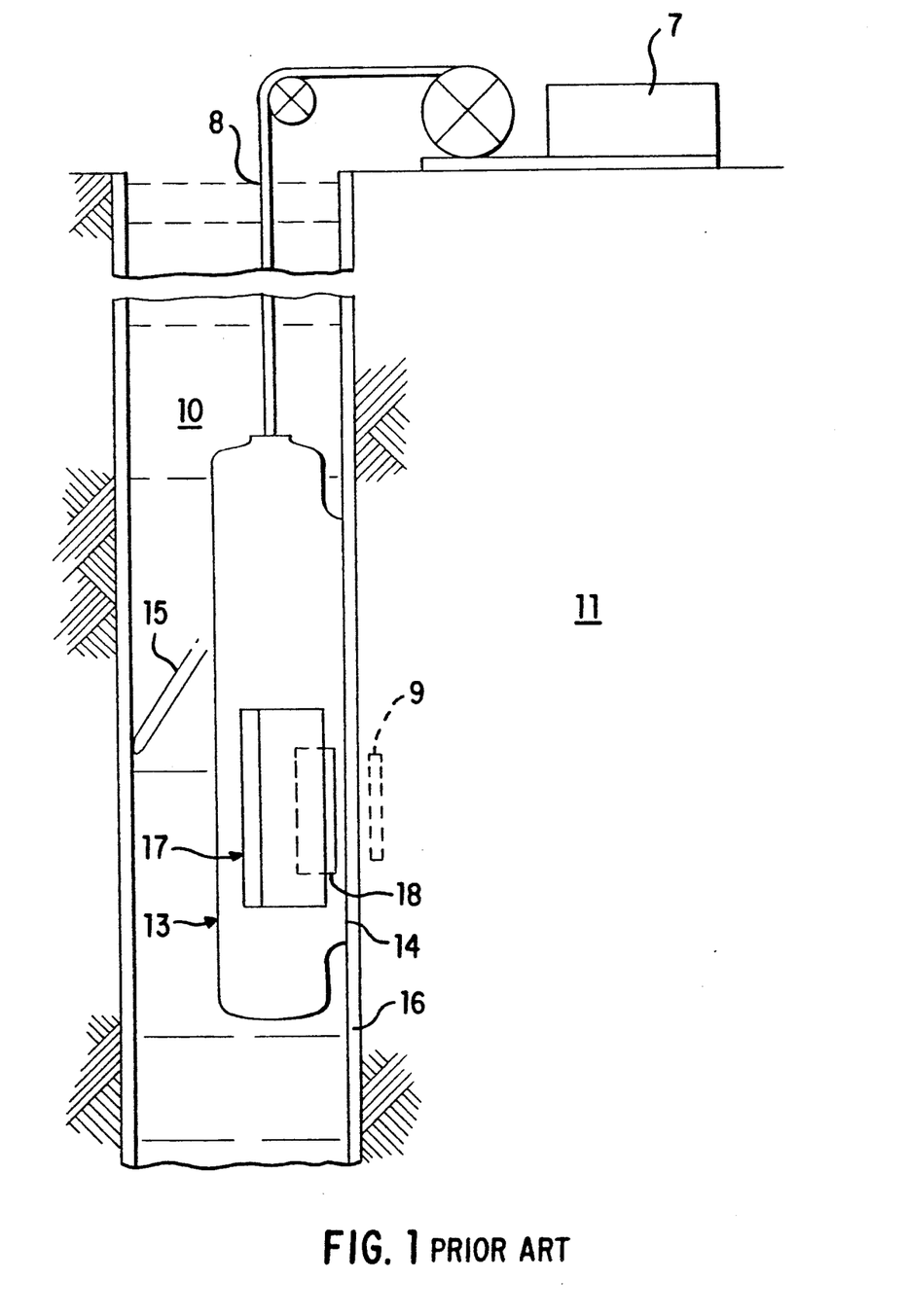
FIG. 1 is a diagram, partially in block form, of a prior art NMR logging apparatus.

Even in ideal conditions, the accurate measurement of these phenomena requires sensitive equipment. Measurements of NMR characteristics of rock samples can be made in a laboratory with reasonable accuracy, but the making of comparable measurements in an earth borehole is rendered more difficult by the hostile environment where temperatures may reach several hundred degrees Fahrenheit, pressures may reach thousands of p.s.i. and all of the equipment must be packed within a cylindrical volume of only several inches in diameter. An improved well logging apparatus for measuring NMR characteristics is set forth in U.S. Pat. No. 4,933,638, assigned to the same assignee as the present application. Reference can be made to said U.S. Pat. No. 4,933,638 for a description of prior art NMR logging approaches. The improved logging apparatus of said patent is summarized in conjunction with FIG. 1–3. In FIG. 1, a borehole 10 is shown adjacent to formations 11, the characteristics of which are to be determined. Within borehole 10 is a logging tool 13 in accordance with the referenced U.S. Pat. No. 4,933,638, which is connected via a wireline 8 to surface equipment 7. Tool 13 has a face 14 shaped to intimately contact the borehole wall, with minimal gaps or standoff, and a retractable arm 15 which can be activated to press the body of the tool 13 against the borehole wall during a logging run, with the face 14 pressed against the wall's surface. A mudcake 16 is shown on the borehole wall. As described in the referenced patent, although the tool 13 is shown as a single body, the tool may alternatively comprise separate components such as a cartridge, sonde or skid, and the tool may be combinable with other logging tools. Also, while a wireline is illustrated, alternative forms of physical support and communicating link can be used, for example in a measurement while drilling system. The tool 13 includes a magnet array 17 and an antenna 18 positioned between the array 17 and the wall engaging face 14. Magnet array 17 produces a static magnetic field $B_0$ in regions surrounding the tool 13. The antenna 18 produces, at selected times, an oscillating magnetic field $B_1$ which is focussed into formation 12, and is superposed on the static field $B_0$ within those parts of formation opposite the face 14. The "volume of investigation" of the tool, shown in dotted lines in FIG. 1, is a vertically elongated region directly in front of tool face 14 in which the magnetic field produced by the magnet array 17 is substantially homogeneous and the spatial gradient thereof is approximately zero. As described in the referenced patent, the tool 13 makes a measurement by magnetically tipping the nuclear spins of particles in formation 12 with a pulse of oscillating field $B_1$, and then detecting the precession of the tipped particles in the static, homogeneous field $B_0$ within the volume of investigation over a period of time.

Figure 2:
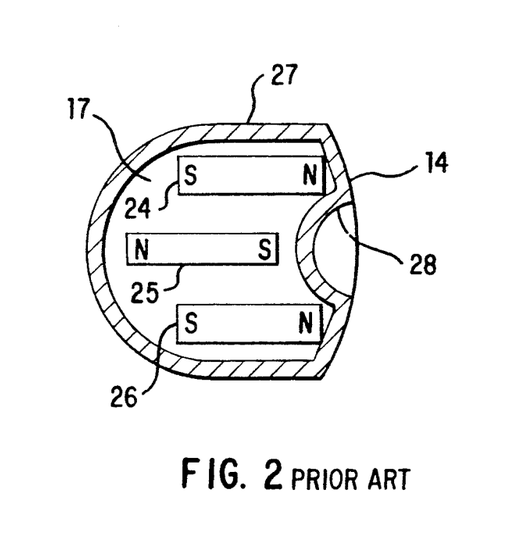
FIG. 2 is a cross-sectional view of a magnet assembly of the FIG. 1 apparatus.

FIG. 2 shows a magnet array 17 disclosed in an embodiment of the referenced patent. The magnet array includes three permanent magnets 24, 25, 26, which are mounted parallel to each other within a metal alloy body 27. The body 27 should be of a material having low magnetic permeability, so as to not interfere with the static magnetic field. Magnets 24, 25, 26 are elongated in the longitudinal direction of the borehole. The magnetic poles of each magnet are not on the smallest faces of the slab, commonly viewed as the ends of a bar magnet; instead, the poles appear on the two opposing edges of the slab magnet and point to the left and right, respectively. Therefore, within the formation 12, the magnetic field $B_0$ surrounding the magnets remains fairly constant along the longitudinal direction of the borehole axis. In the illustration of FIG. 2, magnets 24, 26 are symmetrically mounted in the two sides of the body 27 with the north poles facing the same directions. Magnet 25 is positioned parallel to and between the other two magnets, but with its north poles facing oppositely from magnets 24, 26. Magnet 25 is also shifted slightly away from face 14, relative to magnets 24, 26. The north poles of magnets 24, 26 point in the direction of the face 14 of the tool, while the north pole of magnet 25 is pointed away from the face 14. The central magnet may alternatively be reversed or omitted.

Figure 3:
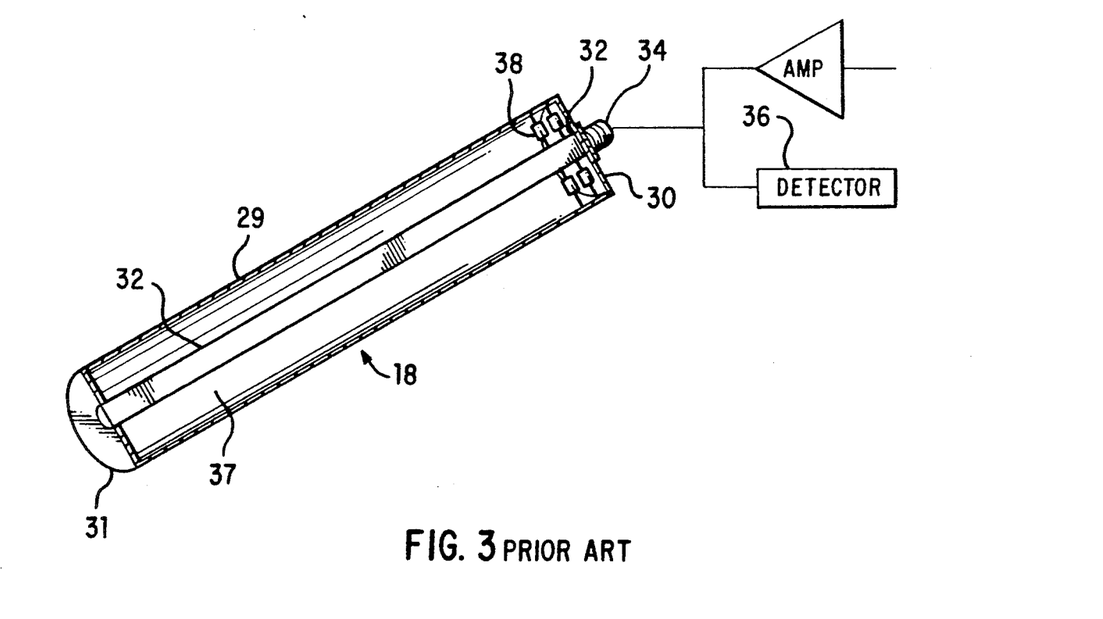
FIG. 3 is a perspective view, partially in block form, of the antenna of the FIG. 1 apparatus.

As described in the referenced patent, the metal body 27 has, on the front face 14 thereof, a semi-cylindrically shaped cavity or slot 28 which faces formations engaged by the face 14. The cavity 28 is adapted for receiving an RF antenna 18 that is shown in FIG. 3. The antenna is positioned outside of the metal body 27 (FIG. 2) of the tool, and is thereby shielded from electromagnetic communication with regions of the borehole which lie behind the body 27, or regions of other formations in directions intercepted by the body 27. Antenna 18 is thus responsive only to magnetic fields originating in front of the wall engaging face 14, e.g. fields originating in the formation 12 or in the mudcake or mud which contacts face 14 in the vicinity of the antenna 18. In a disclosed embodiment of the referenced patent, the body 27 is made of metal alloy sheathing, rigidly attached to interior metal bracing, which envelops most components of the tool other than the antenna 18, including the circuitry, the magnet array 17, and the hydraulics system of the arm 15. The patent points out that the body 27 can alternatively be constructed of other materials, so long as the overall structure is sufficiently strong and the magnetic field of the magnet array 17 can penetrate the body and enter the adjoining formation 12.

In the referenced patent, antenna 18 is used both as an RF transmitter to produce an oscillating magnetic field in formation 12, and as a receiving antenna to detect coherent magnetic signals emanating from precessing protons immediately after the oscillating field is terminated. The antenna serves effectively as a current loop which produces an oscillating field $B_1$ within the volume of investigation that is perpendicular to $B_0$. The antenna 18 comprises a highly conductive semi-cylindrical cavity or trough 29, end plates 30, 31 and center conductor or probe 32 which extends from one end plate 30 to the other end plate 31, parallel to and centered in the semi-cylindrical trough 29. The trough 29, end plates 30, 31 and antenna probe element 32 are indicated as preferably being made of heavy gauge copper which has very low electrical resistance. Antenna probe element 32 is insulated from end plate 30 by a non-conducting bushing 33 and is connected to a conductor 34 on the other side of end plate 30. Probe 32 is attached at its other end to the other end plate 31 so that current passes freely between trough 29 and probe 32 via end plate 31. Conductor 34 is shown in FIG. 3 schematically as being connected to circuitry including an amplifier 35 and a detector 36. All connections in antenna 18 are stated to be brazed or silver soldered, to ensure a suitably low resistive loss. As described in the referenced patent, RF antenna 18 can be driven by amplifier 35 during specified periods of time (the signal being applied at conductor 34 with respect to the antenna body), during which it serves as an RF antenna transmitter. Alternatively, at other specified times, antenna 18 is electronically connected to detector 36, during which time it serves as an RF receiving antenna. In some modes of operation, antenna 18 may be called upon to alternately function as transmitter or receiver in very rapid succession. The space between trough 29 and antenna element 32 is stated to be preferably filled with a ferrite. Several tuning capacitors 38 are connected between the base of antenna element 32 and the trough 29, with the capacitances thereof being chosen to produce an LC circuit, with the resonant frequency being the Larmor frequency. Reference can be made to the U.S. Pat. No. 4,933,638 for further disclosure regarding dimensions of the antenna, the signal-to-noise ratio of signals detected by the antenna, and other details.

It is among the objects of the present invention to provide an improved antenna useful in the described type of logging device and other logging devices. It is also among the objects of the present invention to provide improved wear plates for the described type of logging device and other logging devices.

SUMMARY OF THE INVENTION

The radio frequency antenna of the described NMR logging device must operate with very high sensitivity to the received signal. The antenna is required to sense magnetic fields at a frequency of the order of 1 MHz and a magnitude of about $10^{-12}$ Tesla. The resultant voltage induced on the antenna is of the order of $10^{-8}$ Volts. This tiny voltage must be sensed within about $10^{-4}$ seconds of the cessation of the driving signal on the antenna which will typically have an amplitude of hundreds of volts. When in use as a transmitter, the antenna should produce the largest possible field for a given amount of input power. All of these difficult requirements necessitate use of a high performance antenna, as will be set forth.

As described in the Background portion hereof, a high magnetic permeability non-metallic insulating material, such as a ferrite, is loaded in the antenna in order to increase antenna sensitivity. Applicant has found, however, that the effectiveness of the ferrite is greatly reduced by the strong static magnetic field, which can saturate the ferrite and reduce its intrinsic permeability. In accordance with a feature of the present invention, an antenna housing or shell of high magnetic permeability material is utilized, and effectively provides a shunt path for the static magnetic field in the region of the antenna that would otherwise have a deleterious effect on the ferrite and on antenna operation. In a disclosed embodiment, the antenna shell is formed of a high magnetic permeability metal, such as a mild steel. [As used herein, a high magnetic permeability material means a material having a magnetic permeability of at least 500, mild steel having a magnetic permeability of the order of 1000.] The antenna shell provides foundation support for the conductor metal of the antenna body (which is relatively thin, as will be described), and serves as a low magnetic reluctance path that effectively shunts magnetic fields that could otherwise saturate the ferrite loaded in the antenna.

A further feature of the invention addresses vibrations which Applicant has found to have a serious effect on the performance of an antenna of a logging device. A long standing problem in above-ground nuclear magnetic resonance work has been the magnetoacoustic ringing of metal parts upon radio frequency electromagnetic excitation. This is the so-called "coil disease" [see Clark, Review of Scientific Instruments 35,316 (1965)]. The ringing can be excited in a number of ways. In the simplest case, two conductors carrying currents in opposite directions will repel each other. Similarly, conductors carrying current in the same direction will attract each other. Upon cessation of the current, the force vanishes, and the conductors may vibrate. Another ringing mechanism occurs when a static magnetic field is present. In the presence of the field, a conductor carrying an alternating current will experience an oscillating force at the driving frequency. This force will both drive a gross motion of the conductor, and will generate an ultrasonic wave within the conductor [see Dobbs, in Mason, Thurston, Physical Acoustics v.10 (1973); Kartheuser, Ram Mohan, Rodriquez, Adv Phys 35, 423 (1986)]. Upon cessation of the drive the member will continue to vibrate, and the ultrasonic wave will continue to reverberate.

In the context of a logging device of the type described in conjunction with FIGS. 1-3, any motion of the RF antenna in the static magnetic field will cause a voltage to be developed across it. Other metal structures, such as metal wear plates, can radiate electromagnetic fields which can be sensed by the antenna. Since acoustic vibrations induce signals after the cessation of the transmitter pulse, these spurious signals can overwhelm the desired formation signal. The gross vibrational motion is relatively easy to deal with. It can be restrained and damped by potting the antenna structures with epoxy. The ultrasonic waves, which are more difficult to suppress, are dealt with by a feature of the present invention. In accordance with an aspect of this feature of the invention, the metal structure of the antenna body is selected as having a thickness that will not support ultrasonic resonance modes (compressional or shear) at frequencies related to the transmitted electromagnetic excitation frequency. As will be described, this requires that the metal thickness be less than a particular maximum thickness. However, as will also be described, the metal thickness should preferably be at least a certain minimum thickness so that the metal's resistance does not introduce unacceptable ohmic losses. For example, for a copper antenna body and an excitation frequency of about 2 MHz, the preferred thickness is in the range about 0.1 mm to 0.6 mm.

The relatively thin metal, which is used in the antenna body to minimize undesired ringing, must be supported by more substantial structure. In a disclosed embodiment, the antenna shell serves this purpose, as well as the previously noted purpose of providing a low reluctance shunt path for the static magnetic field. To avoid coupling of any shell vibration to the antenna body, the antenna body is separated from the antenna shell by a medium that has an acoustic impedance that is much different than the acoustic impedance of the body or the shell. The mismatch of acoustic impedance is effective in preventing the undesired coupling of vibration. The preferred thickness of the separating medium is a odd multiple of a quarter of the acoustic wavelength in the separating medium. Applicant has observed that the damping property of the medium itself is much less important than the degree of acoustic impedance mismatch it provides. Thus, for example, tungsten loaded epoxy, which is conventionally used to reduce the Q of piezoelectric ultrasonic transducers, would be a poor choice for use as the separating medium. In a practical antenna it would be too thin to effectively attenuate the sound waves, and it has an acoustic impedance that is not sufficiently dissimilar to that of the metals, so it would provide an undesirably strong acoustic coupling between the metals.

In accordance with a further feature hereof, chip capacitors having surface area contact electrodes, rather than the usual lead contact electrodes, are utilized, and the surface area contacts of each capacitor are respectively coupled to the antenna's metal body and to the metal of the antenna probe. In this manner, resistance in the capacitor path of the antenna circuit is minimized. Applicant has found that lead and contact resistance to the capacitor is a significant factor in the signal-to-noise ratio performance of the antenna. By providing surface area contact electrodes, and no elongated leads, lead and contact resistance is reduced, with a concomitant improvement in signal-to-noise ratio.

In accordance with a described embodiment of the invention there is set forth an apparatus for investigating a characteristic of earth formations traversed by a borehole, including a logging device adapted for longitudinal movement in the borehole. The device includes first means for producing a static magnetic field in the formations and second means for transmitting electromagnetic energy into said formations and for detecting electromagnetic energy from said formations. The second means comprises an antenna assembly which includes an open-ended shell formed of a magnetically permeable material. An open-ended electrically conductive body is disposed within the shell and is spaced therefrom. A medium whose acoustic impedance is substantially different than the acoustic impedance of the shell and the body is disposed between the shell and the body. An electrically conductive probe is disposed in the body, and an electrically insulating magnetically permeable loading material disposed in the body. The shell is formed of a material having a magnetic permeability that is high enough to render the magnetic reluctance of the loading material several times the magnetic reluctance of the shell. The body is formed of a metal having a thickness that is at least several skin depths in said metal at the frequency of the electromagnetic energy and is less than the minimum thickness that would support an acoustic resonance mode in its thickness direction at the frequency of the electromagnetic energy.

Further features and advantages of the invention will become more readily apparent from the following detailed description when taken in conjunction with the accompanying drawings.

DESCRIPTION OF THE PREFERRED EMBODIMENTS

Figure 4:
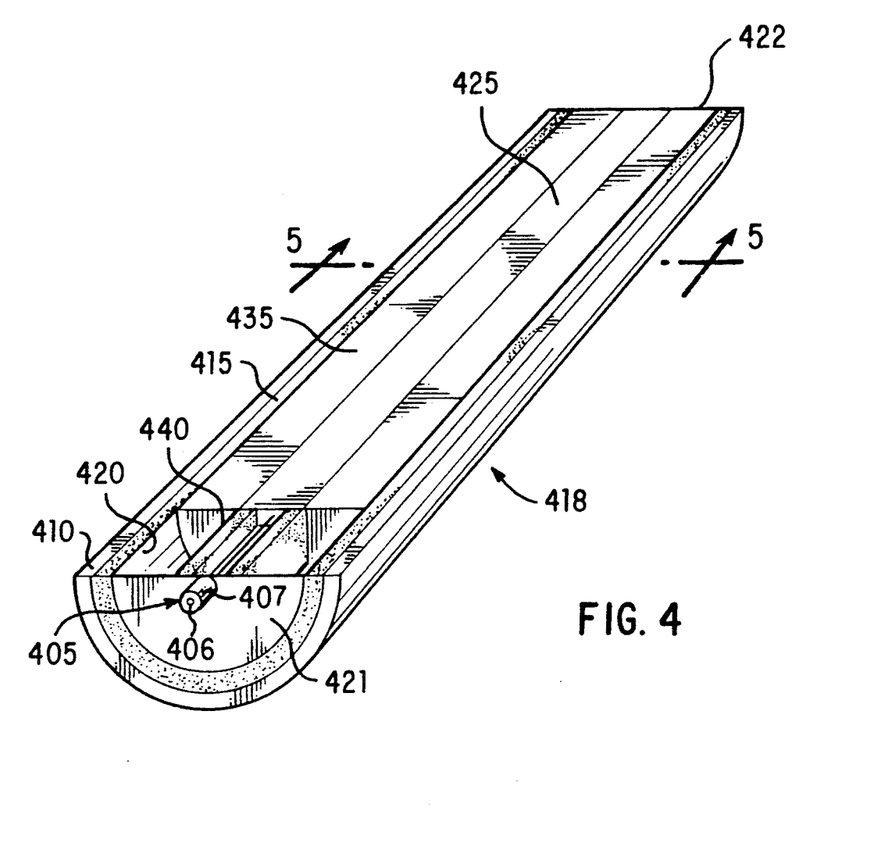
FIG. 4 is a perspective partially broken away view of an antenna assembly in accordance with an embodiment of the invention.
Figure 5:
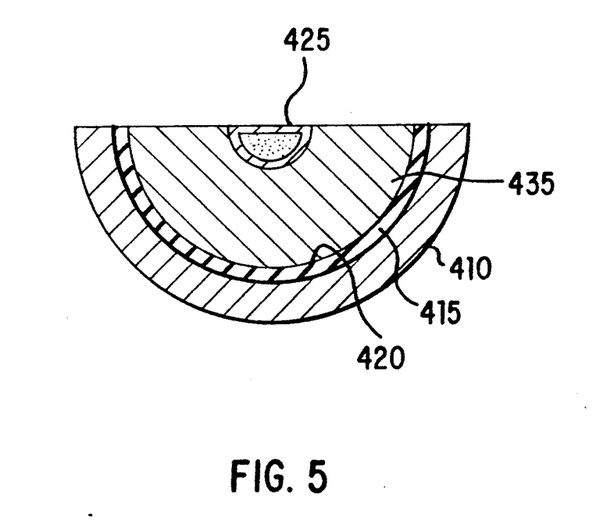
FIG. 5 is a cross-sectional view of the FIG. 4 antenna, as taken through a section defined by arrows 5—5.

Referring to FIGS. 4 and 5, there is shown an embodiment of an improved antenna 418 which can be utilized in the apparatus illustrated in FIGS. 1 and 2 in place of the prior art antenna 18 shown in FIG. 3. It will be understood, however, that the principles of the invention are applicable to other borehole measurement devices and to other antenna configurations. An antenna shell 410 is provided generally in the shape of a half cylindrical trough, and conforming generally to the shape of the depression 28 in the metal alloy magnet casing body 27 (FIG. 2). The shell 410 is formed of a material that preferably has a high magnetic permeability, for example, mild steel.

Disposed on the inner surface of the shell 410 is a layer 415 of neoprene rubber. The material 415, also referred to as a separating medium, preferably has an acoustic impedance that is much different than the acoustic impedance of its adjacent metal structures. Preferably, the acoustic impedance of the material 415 is at least about an order of magnitude less than the acoustic impedance of the adjacent metal structures. For compressional waves, rubber has an acoustic impedance of about $2 \times 10^6$ kg./sm$^2$, whereas steel and copper have an acoustic impedance of about $45 \times 10^6$ kg./sm$^2$. Rubber does not substantially support shear waves. The preferred thickness of the separating medium is an odd multiple of a quarter of the acoustic wavelength in the separating medium. [For thicknesses in a lossy material of greater than a few wavelengths, this relationship is less important.] For example, for neoprene at 2 MHz, the wavelength is about 0.8 mm, so the odd multiples of a quarter wavelength are 0.2 mm, 0.6 mm, 1.0 mm, 1.4 mm, 1.8 mm, etc. A thickness of about 1.4 mm meets this criterion and is considered suitable. It will be understood that the separating medium could alternatively comprise multiple layers of material.

An antenna body or cavity 420 is disposed on the material 415. The antenna body 420 also has a half-cylindrical trough-like shape, and end plates 421 and 422. A probe element 425 extends through the cavity and is coupled to the end plate 422, such as by silver soldering. The other end of the probe 425 is coupled to the center conductor 406 of a coaxial cable 405 which extends through an opening in the end plate 421. The outer conductor 407 of the coaxial cable 405 is coupled to the end plate 421, such as by silver soldering or threaded connector. The coaxial cable is coupled to circuitry of the type first illustrated in FIG. 3 at 35 and 36. The region between the body 420 and the probe 425 is preferably filled with a loading material 435 that is electrically insulating and of high magnetic permeability, for example a ferrite. The probe 425 can be hollow, and filled with a material such as an epoxy. The effectiveness of the ferrite is greatly reduced by the strong static magnetic field, which can saturate the ferrite and reduce its intrinsic permeability. The antenna shell is of high magnetic permeability material, and effectively provides a shunt path for the static magnetic field in the region of the antenna that would otherwise have a deleterious effect on the ferrite and on antenna operation. Preferably, the magnetic reluctance of the ferrite should be several times the magnetic reluctance of the shell. By providing a shell of particularly high magnetic permeability material and of substantial thickness, this condition can be assured.

The antenna body and probe are preferably formed of highly conductive metal, such as copper. As described next, the thickness of the copper is determined in accordance with considerations of minimizing both undesirable acoustic ringing and undesirable ohmic losses.

The thickness modes of a metal plate occur at frequencies given by $$f = nv/2L$$

where n is an integer, v is the shear or compressional sound speed of the material, and L is the thickness of the plate. The compressional speed of rolled copper is 5010 m/s and the shear speed is 2270 m/s. The smallest copper thickness which will support a resonance mode (a shear mode, which has the lower velocity) can be determined using n=1 and v=2270 m/s, and solving for L to obtain $$L = 1.135 \times 10^3 / fm.$$

At a 2 MHz operating frequency, to ensure that the lowest thickness mode of a copper plate is above 2 MHz, the plate should be no thicker than 0.57 mm (0.023").

A thin metal plate will also have modes corresponding to the length and width of plate. The fundamental frequencies of these modes are well below an operating frequency (in this example) of 2 MHz and their very high overtones are not efficiently excited by the spatially uniform magnetic fields.

Due to the very small signal levels to be detected in nuclear magnetic resonance measurements, the antenna should be designed to attain maximum efficiency. One aspect of antenna efficiency involves keeping ohmic losses very low. For this reason, the current carrying surfaces of the antenna must be made of low resistivity metal. Copper or silver are preferred, with copper being the more practical. The conductor metal should be thicker than several times the electromagnetic skin depth at the operating frequency. For copper, the skin depth, in inches, is given by $$\delta = 2.6/f^{\frac{1}{2}}$$

where f is the frequency in hertz. In millimeters, we have $$\delta = 65/f^{\frac{1}{2}} mm.$$

A copper thickness L of three times the skin depth would be $$L = 3\delta = 195/f^{\frac{1}{2}} mm.$$

At an exemplary frequency of 2 MHz one obtains a minimum copper thickness of 0.14 mm (0.0055"). Thus, for a copper sheet antenna body, and an operating frequency of 2 MHz, the copper thickness should be in the approximate range 0.1 mm to 0.6 mm.

Figure 6:
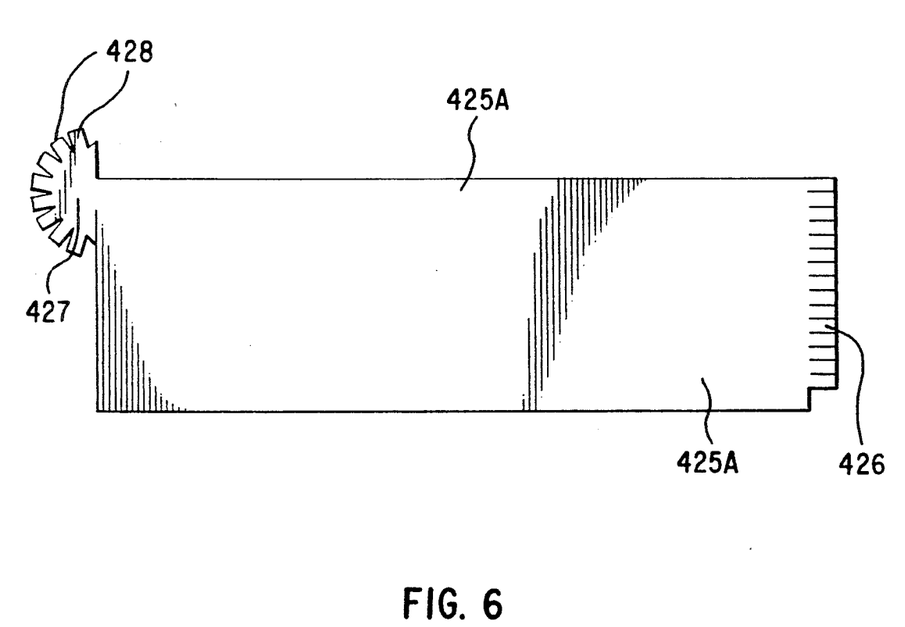
FIG. 6 illustrates metal foil from which the center conductor of the antenna can be constructed.
Figure 8:
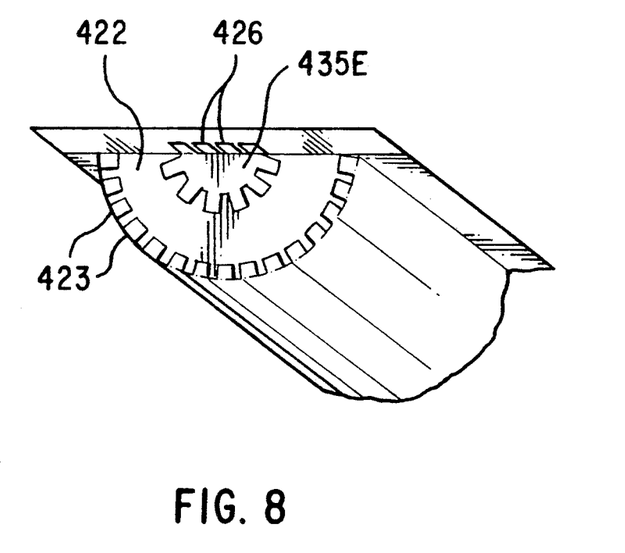
FIG. 8 illustrates a partially broken away outside perspective view of an end of the antenna body during construction.
Figure 9:
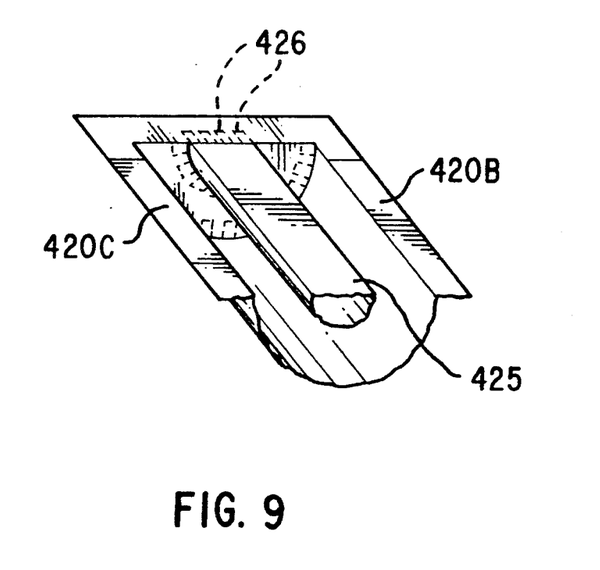
FIG. 9 illustrates a partially broken away perspective inside view of the inside of an end of the antenna body during construction.
Figure 10:
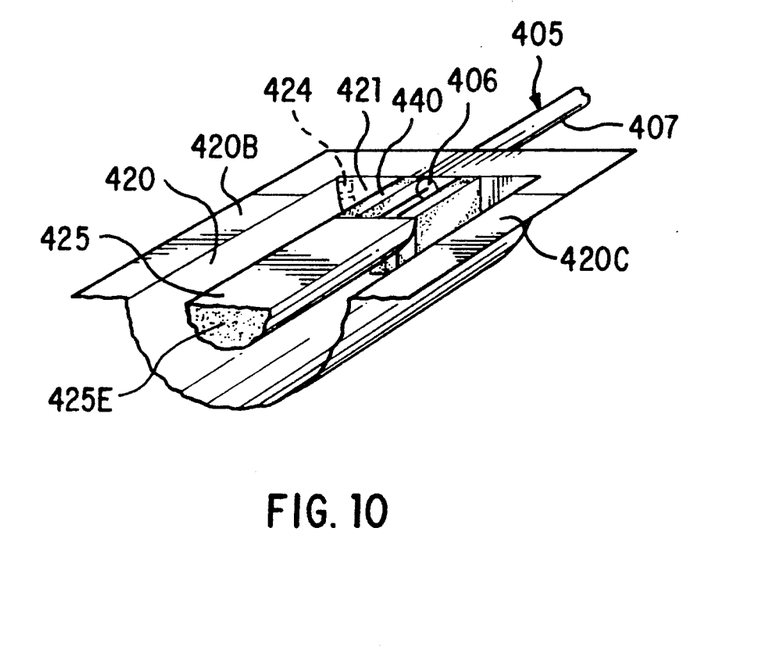
FIG. 10 illustrates a partially broken away perspective inside view of the other end of the antenna body during construction.
Figure 11:
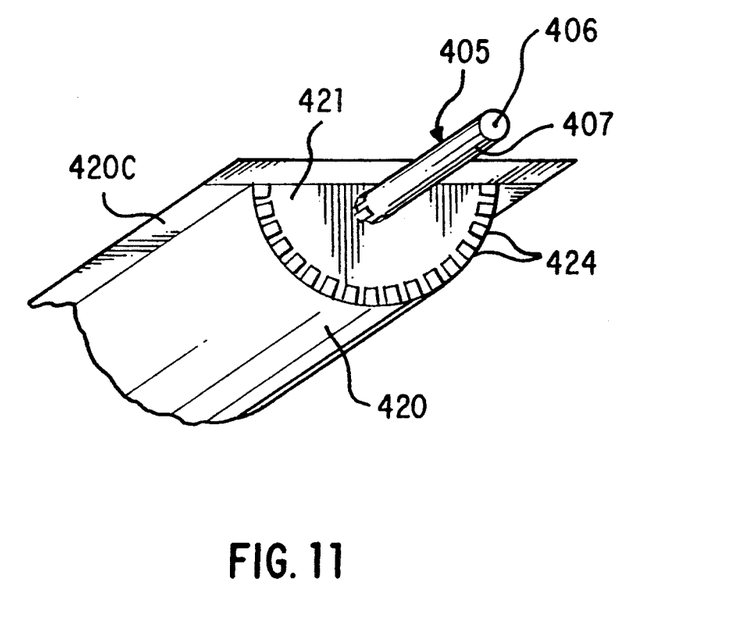
FIG. 11 illustrates a partially broken away outside perspective view of said other end of the antenna body during construction.

There are various ways in which the antenna of the illustrated embodiment can be fabricated. In one example the shell 410 is a ⅛ inch thick half-cylindrical mild steel shell to which brass end plates (not shown) can be silver soldered. The shell is lined with a layer 415 of 1/16 inch thick neoprene rubber which overlays the top edges of the shell. The antenna body 420, with end plates 421, 422 and center conductor 425, is made using sheets of 0.01 inch copper foil which are cut, folded, and soldered as shown in FIGS. 6, 7A–7C, and 8–12. FIG. 6 shows the sheet used to make the center conductor (or probe) 425 of the antenna. The sheet (425A) is folded over a suitably shaped mandrel, the end thereof that is cut with tabs 426 is inserted in aperture 422A of end plate 422 (after folding the tip and side tabs of the end plate shown in FIG. 7B), and the tabs 426 are folded and soldered to the end plate 422, as seen in FIGS. 8 and 9. The other end of sheet 425A includes the end piece 427 and tabs 428 which fold back over the outside of the folded conductor 425A to form the end 427 (FIG. 4) of the center conductor 425 to which the center conductor 40 of the coaxial cable 405 is connected. Tabs of end plate 421 are folded over coaxial cable 405 as shown in FIG. 11. Tabs are soldered to the outer conductor 405.

Figure 7A:
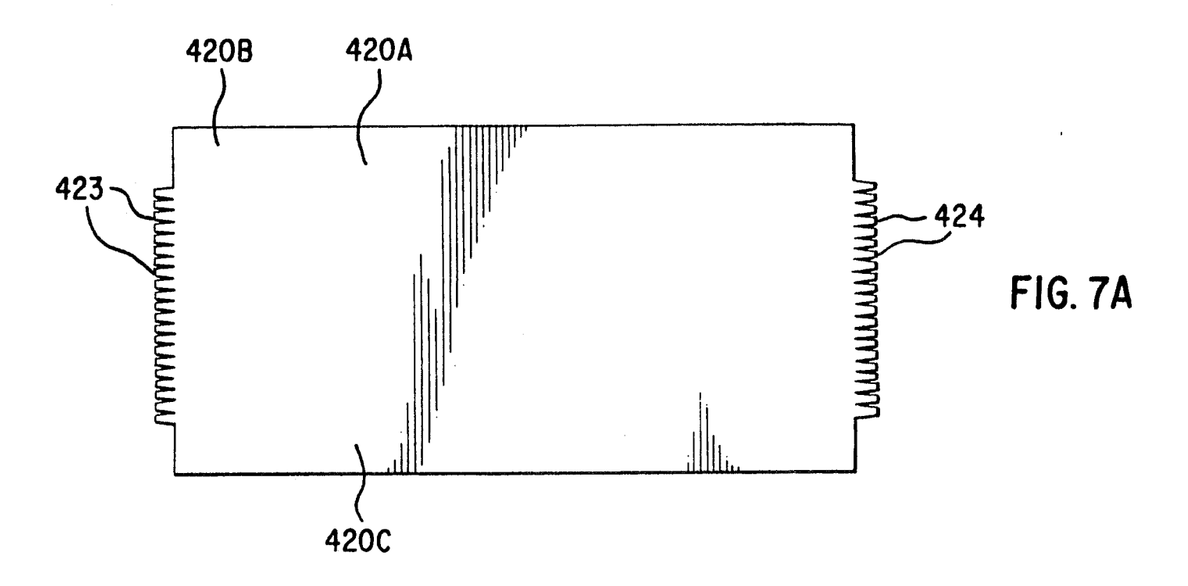
FIGS. 7A, 7B and 7C illustrate metal foil from which the antenna body can be constructed.
Figure 7B:
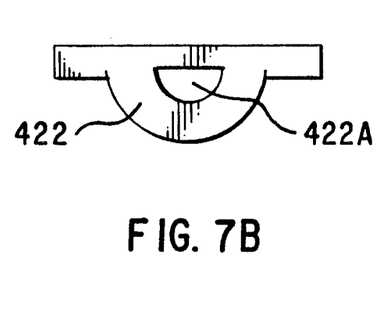
Figure 7C:
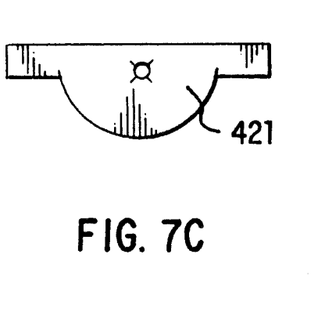
Figure 12:
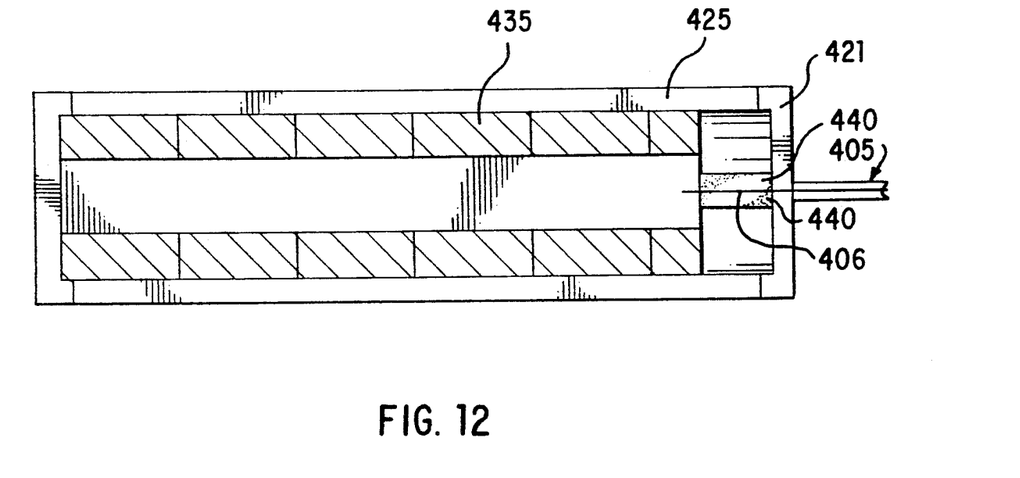
FIG. 12 is a top plan view of the antenna body.

FIG. 7A shows the sheet 420A, with end tabs 423 and 424, which is folded over a cylindrical mandrel and then connected to end plates 422 (FIG. 8) and 421 (FIG. 11) by folding and soldering the tabs 423 and 424, respectively, of sheet 420A to the end plates (after folding the top and side tabs of end plate 421). The folded tabs 420B and 420C, and the folded tabs of the end pieces, reduce bunching of the current at the top edges of the trough. Conformingly shaped blocks of a ferrite material 435 are placed in the structure cavity, as seen in FIG. 12. Suitable ferrite materials are Indiana General "Q1" or Ferroxcube "4C4". The chip capacitors 440 (some of which are shown in FIGS. 4, 10, and 12) are connected between the end plate 421 and the closed end 427 of center conductor 425, with the surface area contacts being soldered to these conductive surfaces to provide very low resistance connections. An electrically nonconductive cementing compound, such as an epoxy, is then poured, preferably under vacuum, into the shell and the center conductor (see 425E in FIGS. 8 and 10), rigidly bonding the parts.

Figure 13:
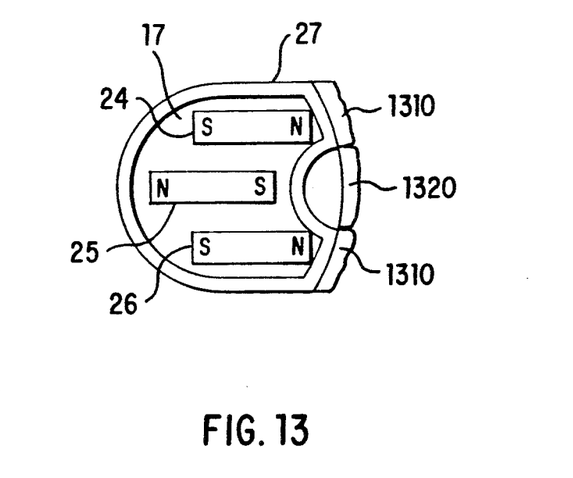
FIG. 13 illustrates positions at which wear plates are typically located.

Another aspect of the present invention relates to wear plates. Wear plates on logging devices are subject to strong shearing stresses and abrasion associated with being dragged along miles of rough borehole under substantial applied pressures. [FIG. 13 illustrates the positions at which wear plates 1310 and 1320 would typically be located with respect to magnet assembly body 27 on the wall-engaging face of a prior art logging device of the type previously illustrated in conjunction with FIGS. 1–3]. The wear plates must not be brittle or they will fracture upon shock. In a nuclear magnetic resonance logging device of the type described herein, magnetoacoustic design of the wear plates is desirable to minimize acoustic ringing. Acoustic modes, of the types previously described, in improperly designed wear plates could dominate the received NMR signal. In particular, thick metal plates, such as are typically used in other borehole logging tools, are not acceptable.

Figure 14:
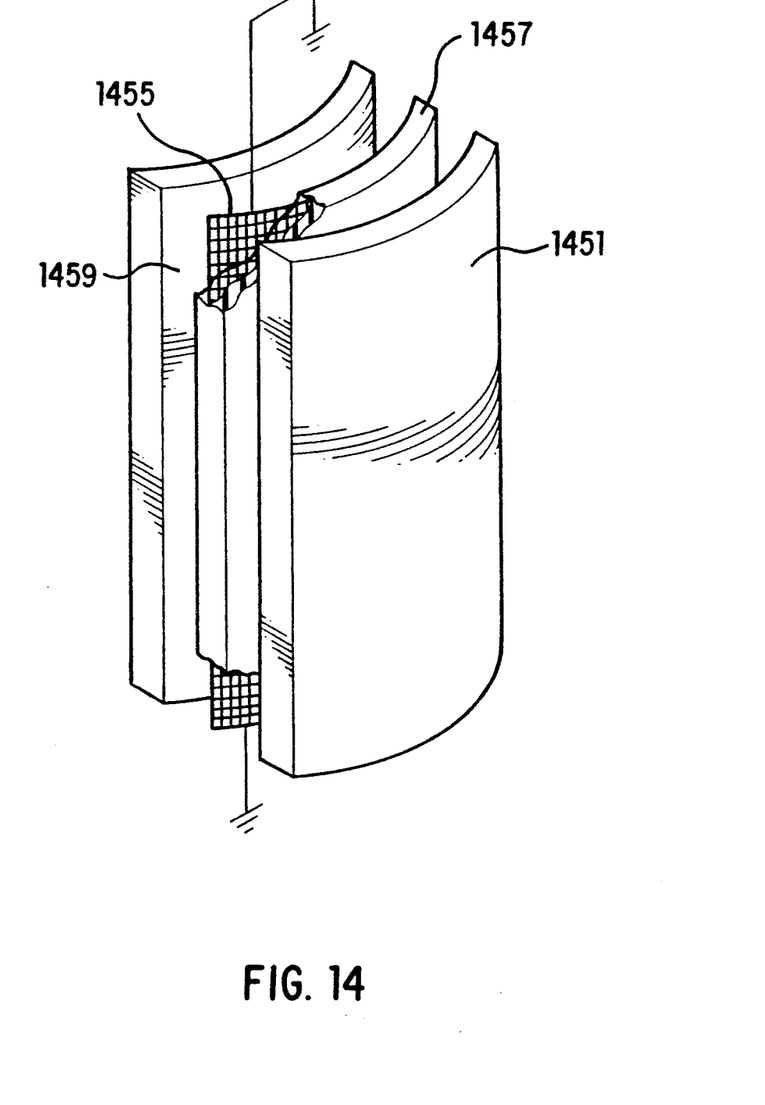
FIG. 14 is an exploded and partially broken away view of a wear plate assembly in accordance with an embodiment of the invention.

In a logging device of the type illustrated in FIGS. 1–3 and FIG. 13, the wear plate 1320 in front of the antenna is preferably a rugged ceramic or plastic with no metal parts that could interfere with signals that are transmitted or received by the antenna. The wear plates 1310 can be provided with an improved structure as illustrated in the embodiment of FIG. 14. A thick layer 1451 of tough non-metallic material forms the wearing surface. Zirconia or composite materials loaded with carbide are suitable for this purpose. On the underside of layer 1451 is a grounded electrically conductive layer 1455 that is electrically and acoustically isolated from its support surface by an insulating medium 1457. The screen 1455 is preferably grounded at two ends as shown in FIG. 14. Suitable ground points are the tabs of the end plates 421 and 422. In a preferred embodiment, the layer 1455 is a copper screen having a multiplicity of small openings therein, and the insulating medium 1457 is rubber impregnating and coating the screen. The screen 1455 prevents the RF field from reaching the magnets or other metal parts and electromagnetically generating sound waves in the manner previously described. At a 1 MHz operating frequency, a screen wire size of about 0.01" is thick enough to support the RF currents, and thin enough not to resonate acoustically. The rubber is a poor acoustical match to the copper and prevents acoustic waves generated in the copper from entering surrounding material and resonating there. The wearing material and screen may be mounted on a metal support plate 1459. The wear plates may be bolted to the logging device. The recessed heads of the bolts can be shielded by plugs made of rubber-impregnated electrically grounded copper screen to minimize acoustic ringing of the bolts, or the bolts can be located at the ends of the plate where the r.f. field is weak.

The invention has been described with reference to particular preferred embodiment, but variations within the spirit and scope of the invention will occur to those skilled in the art. For example, while the invention has been illustrated in a configuration that provides improvement over a particular type of prior art logging device, it will be understood that other configurations can be utilized, consistent with the principles set forth.

We claim:

1. For use in a well logging apparatus wherein a logging device is moveable through an earth borehole and includes means for transmitting electromagnetic energy into formations traversed by the borehole, an antenna assembly supported in said logging device, comprising:

an open-ended shell formed of a relatively thick material;

an open-ended body conforming generally in shape to the inner surface of said shell and being spaced therefrom, said body being formed of an electrically conductive material that is thin relative to the thickness of said shell;

a medium disposed between said shell and said body;

an electrically conductive probe disposed in said body; and means coupled between said body and said probe for receiving electronic signals from said antenna.

2. The antenna assembly as defined by claim 1, wherein the material of said body is a metal having a thickness that is less than the minimum thickness that would support an acoustic resonance mode in its thickness direction at the frequency of said electromagnetic energy.

3. The antenna assembly as defined by claim 2, wherein the material of said body is a metal having a thickness of at least several skin depths in said metal at the frequency of said electromagnetic energy.

4. The antenna as defined by claim 1, wherein said body is formed of copper having a thickness less than $1.135 \times 10^3/f$ m, where f is the frequency of said electromagnetic energy.

5. The antenna as defined by claim 4, wherein said body is formed of copper having a thickness greater than $195/f^{\frac{1}{2}}$ mm., where f is the frequency of said electromagnetic energy.

6. The antenna assembly as defined by claim 1, wherein said shell is formed of a metal, and wherein said medium is a material having an acoustic impedance that is substantially less than the acoustic impedance of the material of said shell and substantially less than the acoustic impedance of the material of said body.

7. The antenna assembly as defined by claim 3, wherein said shell is formed of a metal, and wherein said medium is a material having an acoustic impedance that is substantially less than the acoustic impedance of the material of said shell and substantially less than the acoustic impedance of the material of said body.

8. The antenna assembly as defined by claim 7, wherein said medium is a material having an acoustic impedance that is at least about an order of magnitude less than the acoustic impedance of the material of said shell and the acoustic impedance of the material of said body.

9. The antenna assembly as defined by claim 8, wherein said medium is a material having an acoustic impedance that is at least about an order of magnitude less than the acoustic impedance of the material of said shell and the acoustic impedance of the material of said body.

10. The antenna assembly as defined by claim 1, wherein said medium is rubber.

11. The antenna assembly as defined by claim 3, wherein said medium is rubber.

12. The antenna assembly as defined by claim 6, wherein said medium has a thickness which is an odd multiple of a quarter of the acoustic wavelength of said electromagnetic energy in the separating medium.

13. The antenna as defined by claim 12, wherein said medium is rubber, and said thickness is about 1.4 mm.

14. The antenna as defined by claim 1, further comprising ferrite loaded in said body, and wherein the material of said shell has a magnetic permeability of at least 500.

15. The antenna as defined by claim 3, further comprising a ferrite loaded in said body, and wherein the material of said shell has a magnetic permeability of at least 500.

16. Apparatus for investigating a characteristic of earth formations traversed by a borehole including a logging device adapted for longitudinal movement in the borehole, said device comprising:
first means for producing a static magnetic field in the formations; and
second means for transmitting electromagnetic energy into said formations and for detecting electromagnetic energy from said formations;
said second means comprising an antenna assembly which includes an open-ended shell formed of a magnetically permeable material; an open-ended electrically conductive body disposed within said shell and spaced therefrom; a medium disposed between said shell and said body; an electrically conductive probe disposed in said body; and an electrically insulating magnetically permeable loading material disposed in said body; said shell being formed of a material having a magnetic permeability that is high enough to render the magnetic reluctance of said loading material several times the magnetic reluctance of said shell.

17. Apparatus as defined by claim 16, wherein said second means includes means coupled between said body and said probe for receiving electronic signals from said antenna.

18. Apparatus as defined by claim 16, wherein said loading material disposed in said body comprises a ferrite.

19. Apparatus as defined by claim 16, wherein said shell is formed of a mild steel.

20. Apparatus as defined by claim 18, wherein said shell is formed of a mild steel.

21. Apparatus as defined by claim 16, wherein said shell is formed of a material having a magnetic permeability of at least 500.

22. Apparatus as defined by claim 16, wherein said body is formed of a metal having a thickness that is at least several skin depths in said metal at the frequency of said electromagnetic energy and is less than the minimum thickness that would support an acoustic resonance mode in its thickness direction at the frequency of said electromagnetic energy.

23. Apparatus for investigating a characteristic of earth formations traversed by a borehole, comprising:
a logging device adapted for longitudinal movement in the borehole;
first means, in said device, for producing a static magnetic field in the formations;
second means, in said device, for transmitting electromagnetic energy into said formations and for detecting electromagnetic energy from the formations, said second means comprising an antenna assembly which includes: a trough-shaped shell formed of a magnetically permeable material, said shell being elongated in the longitudinal direction of the borehole; a trough-shaped electrically conductive body, elongated in the longitudinal direction of the borehole, disposed in said shell and spaced therefrom; a medium disposed between said shell and said body; an electrically conductive probe disposed in said body, said probe being elongated in the longitudinal direction of the borehole; an electrically insulating magnetically permeable loading material disposed in said body in the region between the inner surface of said body and said probe;
said second means including means coupled between said body and said probe for transmitting electromagnetic energy via said antenna and for receiving electromagnetic energy via said antenna.

24. Apparatus as defined by claim 23, wherein said body includes electrically conductive side panels at the respective ends of the trough-shaped body, and wherein said probe is connected to one of said side panels.

25. Apparatus as defined by claim 24, wherein said body is formed of copper.

26. Apparatus as defined by claim 23, wherein said body is formed of copper having a thickness less than $1.135 \times 10^3/f$ m, where f is the frequency of said electromagnetic energy.

27. Apparatus as defined by claim 26, wherein said body is formed of copper having a thickness greater than $195/f^{\frac{1}{2}}$ mm., where f is the frequency of said electromagnetic energy.

28. Apparatus as defined by claim 25, wherein the frequency of said electromagnetic energy is about 2 MHz, and wherein the thickness of the copper body is in the range between about 0.1 mm and 0.6 mm.

29. Apparatus as defined by claim 23, wherein said shell is formed of a material having a magnetic permeability that is high enough to render the magnetic reluctance of said loading material several times the magnetic reluctance of said shell.

30. Apparatus as defined by claim 23, wherein said shell is formed of a mild steel.

31. Apparatus as defined by claim 23, further comprising at least one capacitor in said body coupled between said probe and said body, said at least one capacitor having surface area contact regions that are respectively coupled to said probe and to said body.

32. Apparatus as defined by claim 23, wherein said probe comprises a hollow elongated copper tube filled with a non-conductive material.

33. Apparatus as defined by claim 23, wherein said medium is a material having an acoustic impedance that is at least about an order of magnitude less than the acoustic impedance of the material of said shell and the acoustic impedance of the material of said body.

34. Apparatus as defined by claim 23, wherein said medium is rubber.

35. Apparatus as defined by claim 23, wherein said medium has a thickness which is an odd multiple of a quarter of the acoustic wavelength of said electromagnetic energy in the separating medium.

36. Apparatus for measuring nuclear magnetic resonance properties, comprising:
   first means for producing a static magnetic field; and
   second means for transmitting electromagnetic energy and for detecting received electromagnetic energy;
   said second means comprising an antenna assembly which includes an open-ended shell formed of a magnetically permeable material; an open-ended electrically conductive body disposed within said shell and spaced therefrom; a separating medium disposed between said shell and said body; an electrically conductive probe disposed in said body; and an electrically insulating magnetically permeable loading material disposed in said body; said shell being formed of a material having a magnetic permeability that is high enough to render the magnetic reluctance of said loading material several times the magnetic reluctance of said shell.

37. Apparatus as defined by claim 36, wherein said second means includes means coupled between said body and said probe for receiving electronic signals from said antenna.

38. Apparatus as defined by claim 36, wherein said shell is formed of a mild steel.

39. Apparatus as defined by claim 36, wherein said shell is formed of a material having a magnetic permeability of at least 500.

40. Apparatus as defined by claim 36, wherein said body is formed of a metal having a thickness that is at least several skin depths in said metal at the frequency of said electromagnetic energy and is less than the minimum thickness that would support an acoustic resonance mode in its thickness direction at the frequency of said electromagnetic energy.

41. Apparatus as defined by claim 36, wherein said shell is formed of a metal, and wherein said medium is a material having an acoustic impedance that is substantially less than the acoustic impedance of the material of said shell and substantially less than the acoustic impedance of the material of said body.

42. Apparatus as defined by claim 41, wherein said medium is a material having an acoustic impedance that is at least about an order of magnitude less than the acoustic impedance of the material of said shell and the acoustic impedance of the material of said body.

43. For use in a well logging apparatus wherein a logging device is moveable through an earth borehole and includes means for transmitting electromagnetic energy into formations traversed by the borehole and means for receiving electromagnetic energy from the formation; a wear plate assembly mounted on said logging device, and adapted for sliding engagement with the borehole wall, comprising:
   a support member mounted on said logging device;
   an electrically conductive layer spaced from said support member;
   a medium disposed between said member and said conductive layer; and
   a non-metallic wear surface disposed over said conductive layer.

44. The wear plate assembly as defined by claim 43, wherein said electrically conductive layer has a thickness that is less than the thickness that would support an acoustic resonance mode in its thickness direction at the frequency of said electromagnetic energy.

45. The wear plate assembly as defined by claim 43, wherein said electrically conductive layer comprises a metal screen having a multiplicity of openings in its thickness.

46. The wear plate assembly as defined by claim 43, wherein said medium comprises rubber.

47. The wear plate assembly as defined by claim 44, wherein said medium comprises rubber, and wherein said screen is impregnated with rubber.

48. The wear plate assembly as defined by claim 43, wherein said electrically conductive layer is formed of copper having a thickness less than $1.135 \times 10^3/f$ m, where f is the frequency of said electromagnetic energy.

49. The wear plate assembly as defined by claim 43, wherein said support member is formed of metal.

50. The wear plate assembly as defined by claim 43, wherein said electrically conductive layer is electrically grounded.

* * * * *